(12) United States Patent
Boyne-Aitken

(10) Patent No.: US 6,840,492 B1
(45) Date of Patent: Jan. 11, 2005

(54) SLIDE CLAMP

(75) Inventor: David E. Boyne-Aitken, Cadnam (GB)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

(21) Appl. No.: 10/719,828

(22) Filed: Nov. 21, 2003

(51) Int. Cl.$^7$ .................................................. F16K 7/04
(52) U.S. Cl. .................................. 251/7; 251/4; 604/33; 604/249
(58) Field of Search ........................ 251/4, 7; 604/33, 604/249

(56) References Cited

U.S. PATENT DOCUMENTS

| | | | |
|---|---|---|---|
| 2,503,327 A | 4/1950 | Fields | |
| 2,889,848 A | 6/1959 | Redmer | |
| 3,357,674 A | 12/1967 | Coanda | |
| 3,374,509 A | * 3/1968 | Logan et al. | ................ 251/4 |
| 4,248,401 A | 2/1981 | Mittleman | |
| 4,307,869 A | 12/1981 | Mittleman | |
| 4,434,963 A | 3/1984 | Russell | |
| 4,586,691 A | 5/1986 | Kozlow | |
| 4,932,629 A | 6/1990 | Rodomista et al. | |
| 5,017,192 A | * 5/1991 | Dodge et al. | ................ 251/7 |
| 5,290,239 A | 3/1994 | Classey et al. | |
| 5,401,256 A | 3/1995 | Stone et al. | |
| 5,453,098 A | 9/1995 | Botts et al. | |
| 5,593,392 A | 1/1997 | Starchevich | |
| 5,853,398 A | 12/1998 | Lal et al. | |
| 5,967,484 A | 10/1999 | Morris | |

* cited by examiner

Primary Examiner—John Bastianelli
(74) Attorney, Agent, or Firm—Fulwider Patton Lee & Utecht, LLP

(57) ABSTRACT

A slide clamp includes a slot formed in a plate though which a fluid tube is mounted. The tube may be moved to a flow section of the slot or to an occluding section of the slot. Interconnecting the flow and occluding sections is a pinch zone in which the slot is narrower than the occluding section. Because of this narrow slot, the pinch zone resists movement of the tube from either the occluding or the flow sections into another section. The pinch zone includes a pair of curved beams that are formed as a result of apertures formed in the plate at locations laterally outward from the slot of the pinch zone. As a tube is forced from the occluding section to the flow section the curved beams flex outwardly permitting the tube to pass. However, if enough force is not applied to the tube, it will not overcome the curved beams and they will stop movement of the tube. After the tube has passed, the curved beams resiliently return to their rest position once again providing a stop. The beams are symmetrically shaped and will permit movement of the tube in either direction. The apertures also provide identification markers for the slide clamp.

18 Claims, 4 Drawing Sheets

SLIDE CLAMP

BACKGROUND OF THE INVENTION

The present invention relates generally to clamps used to control the flow of medical fluid through an intravenous ("I.V.") tube, and more particularly, to a slide clamp that safeguards against the inadvertent movement of the clamp from an occluding position to a non-occluding position on the tube.

Physicians often desire that medical fluids be delivered to a patient with precision. Therefore, instruments such as infusion pumps are used to regulate the delivery of fluids with a high degree of accuracy. Such infusion pumps provide an occlusion of the fluid line at all times. That is, there is never a direct flow path from fluid source to patient at any time, although the point of occlusion provided by the infusion pump varies. An undesirable situation may occur when fluid is free to flow through the I.V. tube without regulation by the infusion pump or other instrument. This condition is known as a free flow hazard. Activities such as priming of the fluid line or removal of the fluid line from the pump raise the possibility of a free flow hazard. In order to avoid such a free flow situation, a manual clamp may be placed along a portion of the I.V. tube to crimp the tube and occlude the fluid passageway when necessary to stop any flow.

Prior art clamps usable for occluding fluid lines took many different forms, including the commonly known roller clamps and slide clamps. An example of a roller clamp is shown in U.S. Pat. No. 3,802,463. Slide clamps are usually less expensive than roller clamps, operate in a different manner, and are useful with automated activation and deactivation mechanisms. Many slide clamps are formed of a plate having a flow regulating slot formed therein through which the fluid line is disposed. The aperture typically has an occluding section and a flow section. An I.V. tube is mounted through the aperture and is slidable in the aperture to the occluding section, at which the tube is occluded, and to the flow section at which position, fluid flow through the tube is not impeded. Even though the occluding section imposes a high degree of friction to hold the tube in the slot in an occluded configuration, the plate remains susceptible to dislodgement from this configuration by an accidental blow or by snagging. If dislodgement were to occur and the tube move from the occluding section and this movement pass undetected by a nurse or other caregiver, then a potentially dangerous free flow hazard may exist.

A solution to accidental dislodgement has been contemplated by the prior art. By making the tube contacting surface of the aperture extend over the entire depth of the slide clamp, a relatively wide surface is left contacting the I.V. tube in an operative position. This provides a significant frictional force to oppose accidental dislodgement of the I.V. tube relative to the slide clamp between the flow section and the occluding section. However, a drawback to this solution is that the increased frictional resistance imparted by this device may make it difficult to move the tube from the occluded section to the flow section and vice versa. Moreover, increased frictional resistance may lead to rupturing of the tube wall after repeated clamping and unclamping by the clamp.

Hence, a need has been recognized by those skilled in the art for an improved slide clamp that will provide a more secure occluding configuration with a fluid line, yet can be more easily moved to a flow position when desired. A need has also been recognized for a simple design that is both less expensive to manufacture yet more effective in operation. The present invention fulfills these needs and others.

INVENTION SUMMARY

The present invention is directed to a slide clamp for controlling the flow of medical fluid through an I.V. tube. The slide clamp includes a pinch zone or necked-down section that resists movement of the tube out of the occlusion section of the clamp unless an increased level of force is applied to the tube.

More particularly, a slide clamp for use with a tube having a fluid passageway comprises a plate having a longitudinal length and a transverse width and a slot disposed within the plate, the slot having a width; the slot comprising a flow section in which the width of the slot is dimensioned to allow free flow of fluid through the fluid passageway when the tube is located in the flow section and an occlusion section in which the width of the slot is dimensioned to prevent free flow of fluid through the fluid passageway when the tube is located in the occlusion section, the slot also comprising a pinch zone interconnecting the flow section and the occlusion section in which the width of the slot has a narrow configuration in which it is less than the width of the slot in the occlusion section, the pinch zone thereby resisting movement of the tube from either the flow section or the occlusion section to another section, wherein the width of the slot of the pinch zone also has an expanded configuration in which it expands to permit movement of the tube through the pinch zone upon application of a threshold force to the tube in the desired direction of movement of the tube, the pinch zone being bi-directional in that the tube may be moved through the pinch zone from either the flow section or the occlusion section.

In further detailed aspects of the invention, the pinch zone is formed such that the width of the slot resiliently returns to the narrow configuration after the tube has passed through the pinch zone. Also, the pinch zone has a length and the tube has a diameter, the length of the pinch zone being less than the diameter of the tube when the tube is located in the pinch zone. The pinch zone is fabricated of a material having low friction surface properties.

In other aspects, the pinch zone comprises a pair of curved beams between which is located the slot wherein the curved beams comprise a first position at which the slot is in the narrow configuration and a second position at which the slot is in the expanded configuration, and the curved beams are formed so as to resiliently move between the first and second positions, whereby the curved beams resist movement of the tube from either the flow section or the occlusion section to another section. A pair of relieved portions is formed in the plate wherein one of the relieved portions is located laterally outward from one of the curved beams and the other of the relieved portions is located laterally outward from the other of the curved beams. The relieved portions located outward of each curved beam comprise rounded holes, the sizes of which are selected to result in curved beams of a desired shape and flexibility, whereby the flexibility of the curved beams determines the threshold of force required on the tube to move through the pinch zone. The curved beams are formed of a deformable material that has a resiliency to regain its original shape after being subjected to a force capable of deforming the material.

In other aspects, the curved beams are symmetric whereby the pinch zone is bilateral in relation to the adjacent flow section and the adjacent occlusion section. A biasing means for biasing the curved beams to the first position is also provided and comprise material of the plate from which the curved beams are formed wherein the curved beams are curved toward one another when the pinch zone is in the narrow configuration, and wherein the curved beams are flexed laterally outward away from one another when the pinch zone is in the expanded configuration.

In yet further aspects of the invention, there is provided a slide clamp for use with a tube having a fluid passageway, the clamp including a plate having a longitudinal length and a transverse width, a slot disposed within the plate having a flow section dimensioned to allow free flow of fluid through the passageway, an occlusion section dimensioned to prevent free flow of fluid through the passageway, and a necked area interconnecting the non-occlusion section and the occlusion section, the necked area comprising a pair of curved beams having a space located therebetween, a first position wherein the space between the curved beams has a width narrower than a width of the occlusion section, and a second position wherein the curved beams flex to expand the width of the space to permit movement of the tube from the flow section to the occlusion section and from the occlusion section to the flow section when the tube is subjected to a force adequate to flex the curved beams, wherein the curved beams being formed so that they flex back to the first position after the tube has moved through the space, and wherein the curved beams resist movement of the tube from the occlusion section to the flow section when the tube is subjected to a force inadequate to flex the curved beams.

Also, the necked area has a flat surface for contacting the tube, wherein the necked area surface is fabricated from a material having low friction surface properties. A surface of the occlusion section for contacting the tube is defined by an edge coming to a point, and the occlusion section surface is fabricated from a material having low friction surface properties. Finally, the plate is made of a deformable and resilient material; the material has a resiliency to regain its original shape after being subjected to a force capable of deforming the material.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

Figure 1:
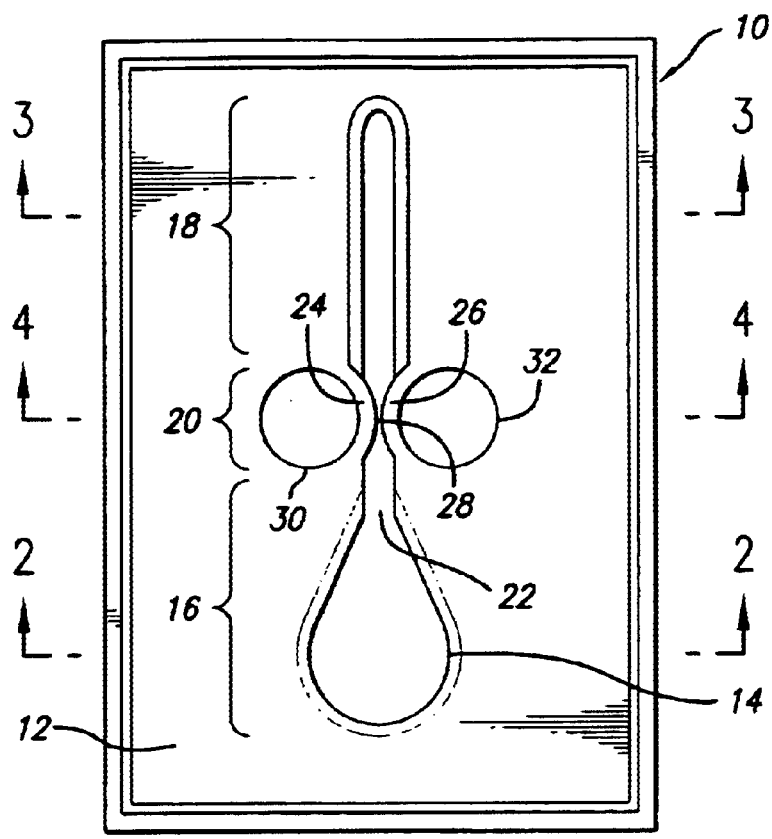
FIG. 1 is a top view of a slide clamp in accordance with aspects of the present invention showing a slot having a flow section, an occlusion section, and a pinch zone interconnecting the two.
Figure 2:
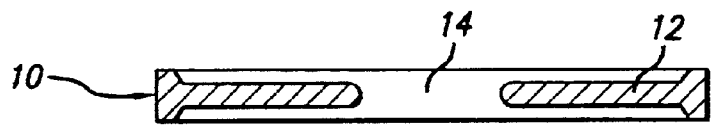
FIG. 2 is a side cross-sectional view of FIG. 1 taken along lines 2—2 showing the flow section of the slot.

Referring now to the drawings in more detail in which like numerals used across several views indicate like or corresponding elements, there is shown in FIG. 1 a slide clamp 10 for controlling the flow of medical fluid through an intravenous (I.V.) tube (not shown) located through the clamp. The clamp includes a plate 12 that forms the body of the slide clamp and a slot 14 formed in the plate. The slot includes a flow section 16, shown in cross-sectional detail in FIG. 2, and an occlusion section 18, shown in cross-sectional detail in FIG. 3. The slot further encompasses a pinch zone 20 located between the flow section and the occlusion section for resisting the accidental dislodgement of the I.V. tube from the occlusion section to help prevent hazards associated with free flow, as discuss above.

The pinch zone 20 appears as a necked down area and provides a slot length of reduced width in comparison to the occlusion section 18 and thus functions as a stop that resists movement of a tube that has been placed in the occlusion section from leaving that section and moving to the flow section 16. The pinch zone of FIG. 1 is bilateral and is located between the occlusion section and the flow section 16 and in the embodiment of FIG. 1 it also resists movement of a tube from the flow section. Yet the stop section is resilient so that its resistance can be overcome by applying increased force to the tube to move the tube into and past the pinch zone in either direction. Because the pinch zone is located between both the occlusion section and the flow section and because it is bilateral, it provides a stop against movement from either section into the other but will allow such movement when sufficient override force has been applied to the tube in the desired direction of movement. Further, because of the resilience of the pinch zone, overcoming its resistance will not permanently or plastically deform the stop section and it will function multiple times.

As shown in FIG. 1, the pinch zone 20 is not only bilateral, but it is also symmetrical. The end of it facing the occlusion section has the same configuration as the end of it facing the flow section. A tapered lead section 22 is placed between pinch zone 20 and the flow section 16 in the embodiment of FIG. 1 although it may be considered to form a part of the flow section. In another case, the tapered lead section may be thought of as forming a part of the pinch zone, in which case the stop section is then not symmetrical.

Considering the pinch zone 20 of FIG. 1 in further detail, a pair of curved beams 24 and 26 has the pinch zone slot 28 located between them. This configuration is shown in more detail in the cross-sectional view of FIG. 4. As briefly discussed above, the pinch zone slot is narrower than both the slot of the flow section 16 and the slot of the occlusion section 18 and therefore provides resistance to movement of a tube located in either section. However, the pinch zone slot nevertheless is a slot through which a tube mounted in the slide clamp 10 may move under the right conditions. In this case, the pinch zone slot is configured to expand to a larger size (expanded configuration) to accommodate passage of a tube when pressure is placed upon the pinch zone slot by a tube being forced into the pinch zone with a force greater than the force holding the pinch zone in the narrow configuration shown in FIG. 1.

To achieve the expandable nature of the pinch zone 20 aperture 28, two apertures are formed laterally outward from the pinch zone on opposite sides of the pinch zone slot. The apertures are round in shape and due to their placement near the pinch zone slot, they form the curved beams 24 and 26. That is, the first curved beam 24 is formed as a result of forming the first aperture 30 laterally outward of the slot. Likewise, the second curved beam 26 is formed by forming the second aperture 32 laterally outward of the slot. The location and size of the apertures form the curved beams as well as determine the amount of force necessary to overcome the beams and expand the pinch zone slot. For example, the thinner the beams, the less force it will require to expand the slot while the thicker the beams, the more force it will require to expand the slot. It should also be recognized that thinner beams provide less of a stop force against a tube in the occlusion section 18 moving to the flow section 16 and are more prone to breakage. Thinner beams provide less protection against the free flow hazard discussed above while thicker beams may require so much force to expand the pinch zone that the tube integrity may be compromised.

The apertures 30 and 32 thus provide a spring-like feature that results in biasing or urging the curved beams 24 and 26 inward to the pinch zone to stop or resist undesired movement of the tube between occlusion section 18 and flow section 16. This is known as the narrow configuration of the pinch zone slot. When the curved beams are at the narrow configuration, pinch zone slot has a width that is narrower than the width of the occlusion section 18. When the pinch zone is in the expanded configuration in which the beams are pressed outwardly, the slot 28 of the pinch zone expands to a wider width to permit the tube to traverse the pinch zone 20.

The curved beams 24 and 26 are integral with the plate 12 since they are formed of the plate due to the apertures 30 and 32, as discussed above. It can be seen by reference to FIG. 1 that the curved beams are rounded inwardly, i.e., towards the pinch zone slot. They therefore present a rounded taper to the pinch zone facing in both directions; i.e., towards the occlusion section and towards the flow section. The pinch zone is therefore bilateral, or two-way, in that a tube can be moved from either the occlusion section into the pinch zone or from the flow section into the pinch zone. Provided that enough force is imparted to the tube in the desired direction of movement, the curved beams will move outwardly to expand the pinch zone slot. Because the curved beams are attached at either end to the plate with the aperture behind their centers, and because the beams are formed of a resilient material, the beams may bend or flex outwardly to the expanded configuration to accommodate the movement of a tube through the pinch zone, yet will return to the narrow configuration shown in FIG. 1 once the tube has passed through the pinch zone due to their resiliency and mounting configuration.

Figure 5:
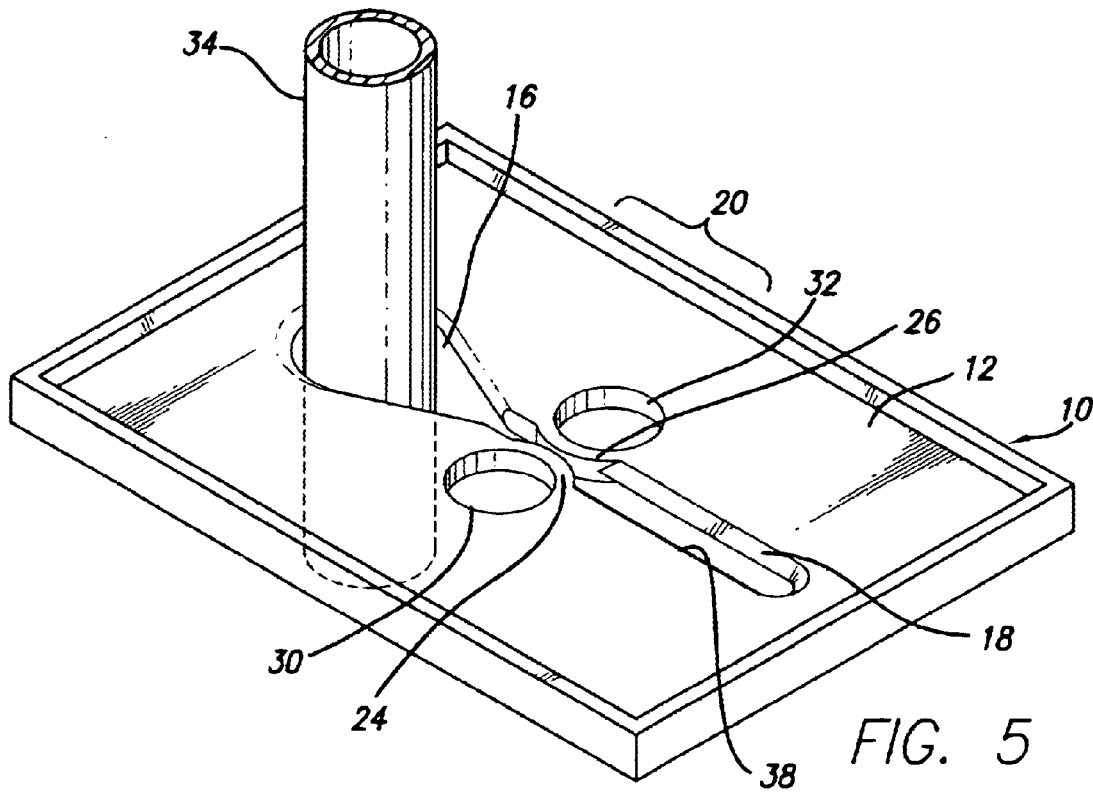
FIG. 5 is a perspective view of a slide clamp in accordance with aspects of the invention showing a tube located in the flow section.
Figure 6:
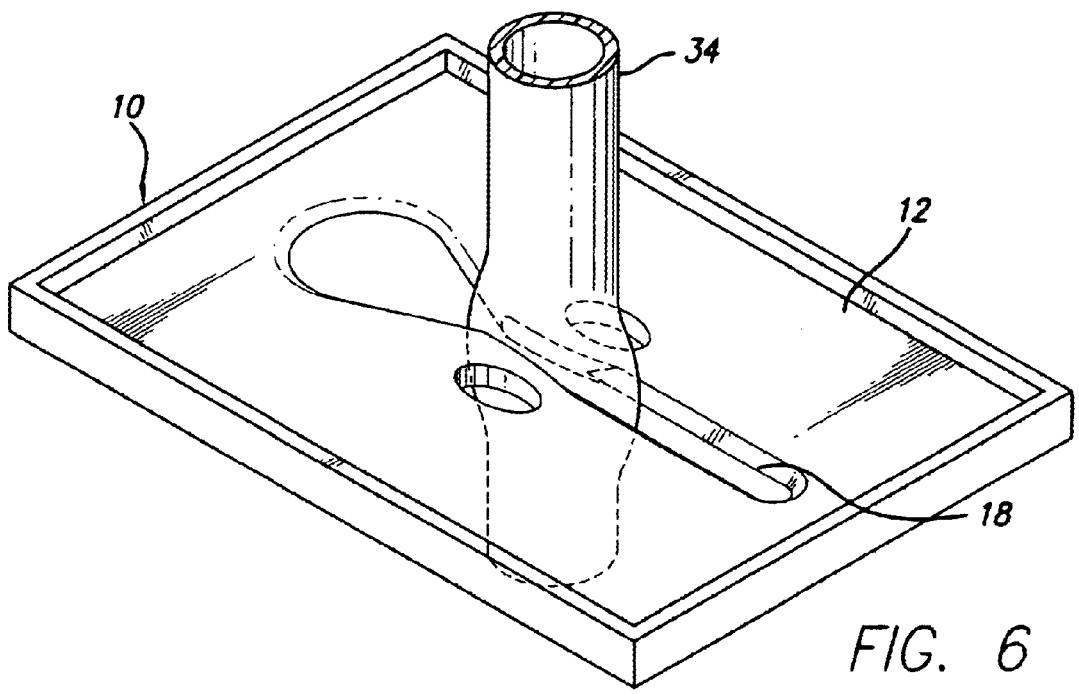
FIG. 6 is a perspective view of a slide clamp in accordance with aspects of the invention showing a tube located in the pinch zone.
Figure 7:
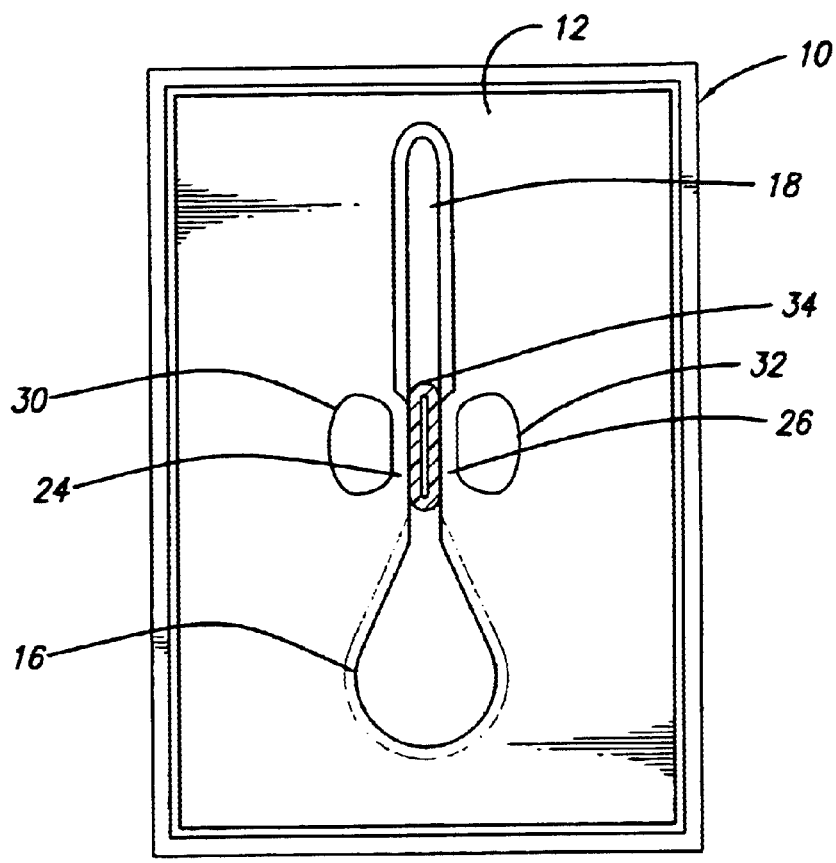
FIG. 7 is a top view of a slide clamp in accordance with aspects of the present invention showing a tube located in the pinch zone with curved beams flexed outward to allow the tube to pass.

The above can be seen by reference to FIGS. 5, 6, 7, and 8. In FIG. 5, an I.V. tube 34 is shown residing in the flow section 16 of the slide clamp 10. When an occlusion is desired, the I.V. tube is moved from the flow section through the pinch zone 20. As shown in FIG. 6, the resilient curved beams 24 and 26 flex or deform outwardly as the tube passes through the pinch zone. The action of the pinch zone can also be seen in the top view of FIG. 7 in which the deformation of the apertures 30 and 32 from circles can be more clearly seen. The curved beams have flexed outwardly such that they appear flattened to accommodate the passage of the tube. It may also be noted from FIG. 7 that the length of the curved beams is less than the diameter of the tube when the tube is flattened as shown. A portion of the inner passage 36 of the tube is actually open and flow may occur. This is acceptable because the tube is either coming from the flow section and moving to the occluding section or vice versa. The purpose of the occluding section is to provide complete occlusion while the pinch zone functions only to resist movement of the tube in either direction within the clamp 10. The function of the occluding section 18 can be seen in FIG. 8 where the tube is completely occluded across its entire diameter. Because the pinch zone 20 need not provide full occlusion of the complete tube diameter, it can be made shorter in length and is easier-to-manufacture.

In the drawings, the apertures 30 and 32 used to form the curved beams 24 and 26 are circular; however, other shapes may be used.

In order to provide an effective pinch zone 20, the curved beams 24 and 26 must have enough resistance against flexing outwardly such that it would take a significantly larger force against the tube than that normally encountered in the ordinary use of the slide clamp to move the tube through the pinch zone. This pinch zone force threshold would normally be set above the force that could be expected from ordinary snagging and accidental blows. As mentioned above, the flexibility of the curved beams is determined by the thickness and width of the beams as well as the material from which the beams are formed. Absent a force above the threshold, any attempt to move the tube out of the occlusion section and back into the flow section would fail.

It should be noted also that after the tube has passed through the pinch zone 20, the beams 24 and 26 flex back to their rest position at which the pinch zone slot is in the narrow configuration. Once again, the pinch zone will provide an effective stop against undesirable movement of the tube 34.

Figure 8:
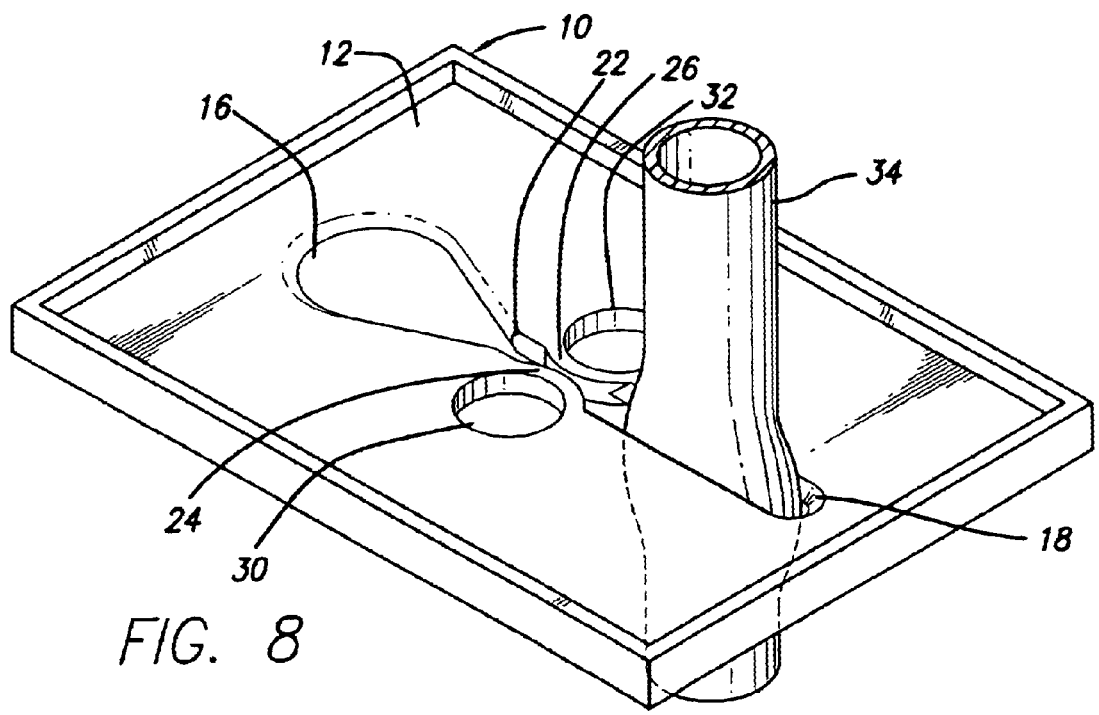
FIG. 8 is a perspective view of a slide clamp in accordance with aspects of the invention showing a tube located in the occluding section.

The plate 12 may be made of a deformable material with the resiliency to regain its original shape after being deformed. It may consist of any plastic material that can be injection molded and possess good elasticity such as, for example, polypropylene, polyvinyl chloride, acrylonitrile butadiene styrene (ABS), or similar materials. Because of this material, the particular configuration of the curved beams, and aided by the presence of the apertures 30 and 32 located outwardly from their corresponding curved beams, the curved beams demonstrate a spring-like characteristic. Thus, when adequate force from the tube 34 is applied to the beams, the beams flex away from the tube permitting the tube to pass into the occlusion section 18. Once the tube has passed the pinch zone, the beams spring back to their original shape, as shown in FIGS. 1 and 8. However, too much resistance to flexing outwardly by the curved beams can have a damaging effect on the wall of the tube. Thus the threshold force should not be set too high.

Figure 3:
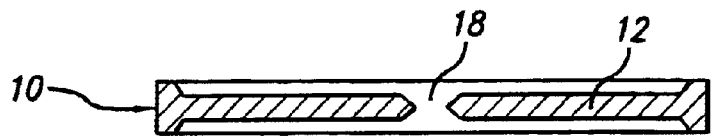
FIG. 3 is a side cross-sectional view of FIG. 1 taken along lines 3—3 showing the occlusion section of the slot.

The occlusion section 18 includes the pointed surface 38, seen in cross section in FIG. 3. This pointed surface contacts the tube 34 and applies sufficient force to crimp the wall of the tube. This results in an occlusion wherein all liquid flow through the tube is stopped. Such an edge reduces the surface area contacting the tube to thereby reduce the frictional force exerted on the tube as it is moved from the flow section 16 to the occlusion section 18 and vice versa. Because of reduced frictional force, moving the tube within the slide clamp 10 is less difficult than it would be if the contacting surfaces of the occlusion section had a larger surface area. Further, the surfaces of the occlusion section contacting the tube may be fabricated from a material having low-friction surface properties such as Teflon, Delrin, Kel-F, or any other suitable material. A material having low friction surface properties helps eliminate difficulty in moving the tube within the occlusion section. Moreover, the lower frictional forces created when the tubing is crimped between the surfaces reduces the tendency of cutting or of substantially weakening the tubing wall at the point of repeated crimping.

Figure 4:
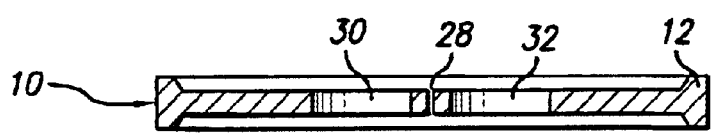
FIG. 4 is a side cross-sectional view of FIG. 1 taken along lines 4—4 showing the pinch zone of the slot.

In a preferred embodiment, the surfaces of the pinch zone 20 contacting the tube 34 are flat as shown in FIG. 4 to avoid shearing the tube wall as it is moved through the pinch zone should repetitive movement of the tube in the slide clamp be necessary. As mentioned above, complete occlusion of the tube is not the function of the pinch zone. To further avoid shearing or damage to the tube wall, the surfaces of the pinch zone contacting the tube 32 may also be fabricated from a material having low-friction surface properties such as Teflon, Delrin, Kel-F, or any other suitable material.

Hence, an infusion set utilizing the clamp of the present invention may successfully control fluid flow through an I.V. tube by manipulating the clamp and tube as stated above. Unlike many prior art clamps, the clamp of the present invention safeguards against the undesirable situation where a tube is inadvertently dislodged from an occluding position. Here, the situation may occur when the tube 34, already in the occlusion section 18, receives inadvertent force against it in the direction of the flow section 16 of the slot. Such inadvertent force may result from an accidental blow or snagging. Without the safeguard of the pinch zone, the tube may well move to the flow section of the slide clamp 10 where fluid flow is uncontrolled. However in accordance with aspects of the invention, the pinch zone blocks unintentional movement of the tube 34 toward the flow section 16 thus preventing the possible hazard associated with unexpected free flow.

Figure 9:
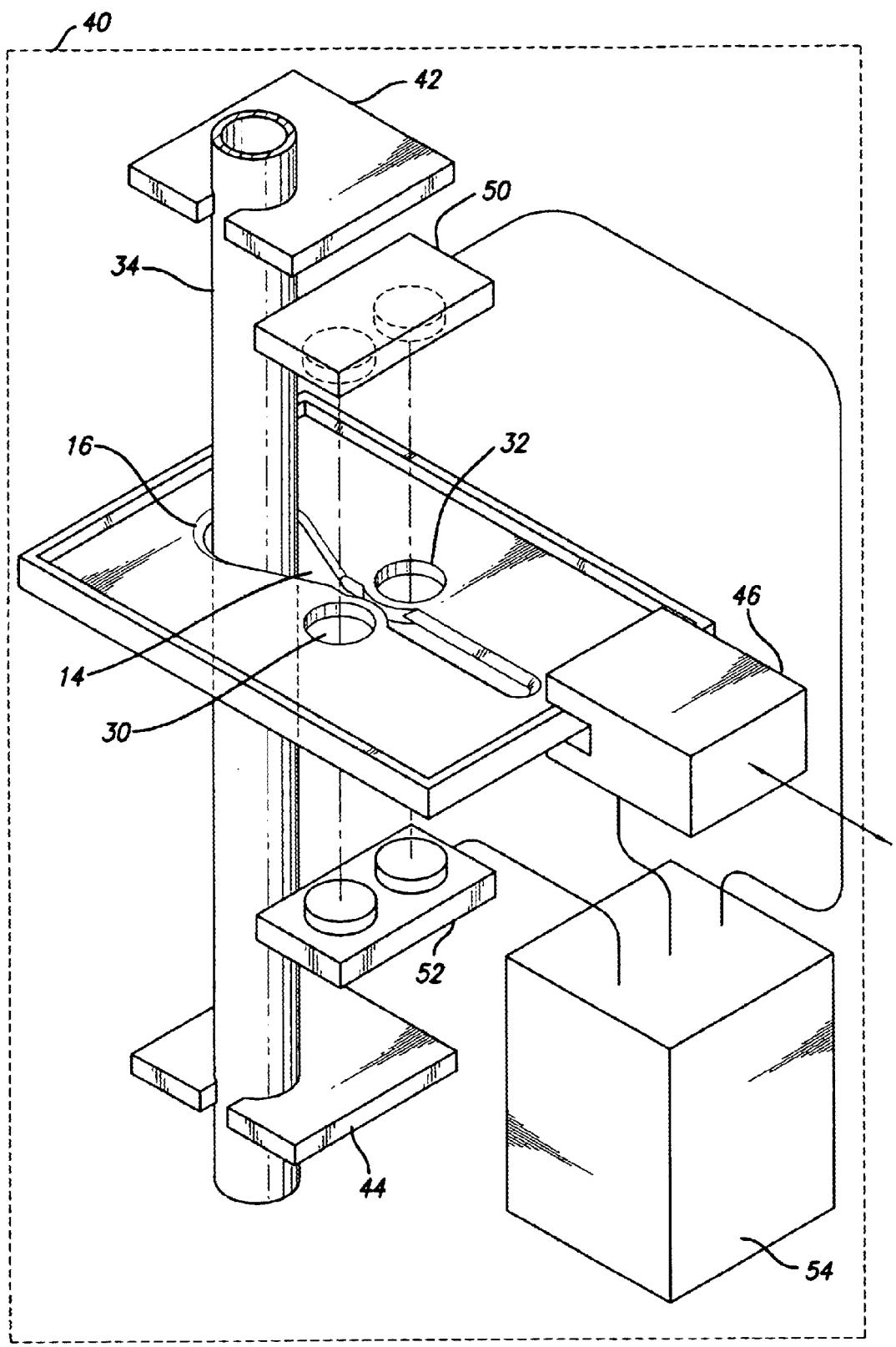
FIG. 9 is a perspective view of a slide clamp in accordance with aspects of the invention showing a tube located in the flow section of the slot, a mechanism for holding the tube in position as the slide clamp is moved in relation to the tube, a mechanism for moving the slide clamp, and a detector system for sensing the existence of the two relieved portions of the plate to identify the slide clamp.

While the slide clamp 10 may be moved manually across the tube to achieve the desired flow or non-flow configuration of the tube, a mechanism may also be used. FIG. 9 presents a system view of the use of the slide clamp in which it functions in a medical instrument 40. As before, a tube 34 is engaged in the slide clamp, in this case, in the flow section 16 of the slot 14. The tube is anchored above and below the slide clamp with tube anchors 42 and 44. The slide clamp is engaged with a slide clamp controller 46 that controls the position of the slide clamp in relation to the tube. In one case, the tube anchors hold the tube stationary while the slide clamp is moved in relation to the tube by the slide clamp. In this case, the slide clamp controller has just moved the slide clamp to the right to allow flow through the tube. When the flow is completed and the tube is to be removed from the instrument, the slide clamp controller will then move the slide clamp to the left to occlude the tube before it is removed from the instrument. In another embodiment, the slide clamp controller remains stationary and the tube anchors move the tube towards or away from the slide clamp to permit or stop flow through the tube as desired.

A slide clamp identification system 48 is also provided in which transmitters 50 transmit beams of energy through the apertures 30 and 32 of the slide clamp 10. Sensors 52 located on the opposite side of the slide clamp detect the beams and convey their signals to a processor 54. The processor monitors the transmitters and the sensors and based on receiving or not receiving detection signals from the sensors, identifies the slide clamp or determines that it is not appropriate for use in the instrument 40. The processor may also control the slide clamp controller 46. Many details have not been included in this discussion to preserve clarity. For example, another detector system may be used to determine that a slide clamp, any slide clamp, has been inserted into the instrument. A display or audio device may be provided to communicate information concerning the identification of lack of identification of the slide clamp. The clamp controller 46 may not function if the processor determines that the slide clamp cannot be identified.

Although the invention has been described in terms of preferred structures, it will be apparent to one skilled in the art that obvious modifications may be made without departing from the invention. It is intended that all such modifications are included in the spirit and scope of the invention as defined herein and protected by the appended claims.

What is claimed is:

1. A slide clamp for use with a tube having a fluid passageway, the slide clamp comprising:

a plate having a longitudinal length and a transverse width; and a slot disposed within the plate, the slot having a width;

the slot comprising a flow section in which the width of the slot is dimensioned to allow free flow of fluid through the fluid passageway when the tube is located in the flow section and an occlusion section in which the width of the slot is dimensioned to prevent free flow of fluid through the fluid passageway when the tube is located in the occlusion section;

the slot also comprising a pinch zone interconnecting the flow section and the occlusion section in which the width of the slot has a narrow configuration at which the width of the slot is less than the width in the occlusion section, the pinch zone thereby resisting movement of the tube from either the flow section or the occlusion section to another section, the slot of the pinch zone also having an expanded configuration at which the width of the slot expands to permit movement of the tube through the pinch zone upon application of a threshold force to the tube in the desired direction of movement of the tube, the pinch zone being bi-directional in that the tube may be moved through the pinch zone from either the flow section or the occlusion section.

2. The slide clamp of claim 1 wherein the pinch zone is formed such that the width of the slot resiliently returns to the narrow configuration after the tube has passed through the pinch zone.

3. The slide clamp of claim 1 wherein the pinch zone has a length and the tube has a diameter, the length of the pinch zone being less than the diameter of the tube when the tube is located in the pinch zone.

4. The slide clamp of claim 1 wherein the pinch zone is fabricated of a material having low friction surface properties.

5. The slide clamp of claim 1 wherein the pinch zone comprises:

a pair of curved beams between which is located the slot of the pinch zone;

wherein the curved beams comprise a first position at which the slot is in the narrow configuration and a second position at which the slot is in the expanded configuration; and the curved beams are formed so as to resiliently move between the first and second positions;

whereby the curved beams resist movement of the tube from either the flow section or the occlusion section to another section.

6. The slide clamp of claim 5 further comprising a pair of apertures formed in the plate wherein one of the apertures is located laterally outward from one of the curved beams and the other of the apertures is located laterally outward from the other of the curved beams.

7. The slide clamp of claim 6 wherein the apertures located outward of each curved beam comprise rounded holes, the sizes of which are selected to result in curved beams of a desired shape and flexibility;

whereby the flexibility of the curved beams determines the threshold of force required on the tube to move through the pinch zone.

8. The slide clamp of claim 5 wherein the curved beams are formed of a deformable material that has a resiliency to regain its original shape after being subjected to a force capable of deforming the material.

9. The slide clamp of claim 5 wherein the curved beams are symmetrical;

whereby the pinch zone is bilateral in relation to the adjacent flow section and the adjacent occlusion section.

10. The slide clamp of claim 6 further comprising a biasing means for biasing the curved beams to the first position.

11. The slide clamp of claim 10 wherein the biasing means comprise material of the plate from which the curved beams are formed;

wherein the curved beams are curved toward one another when the pinch zone is in the narrow configuration;

wherein the curved beams are flexed laterally outward away from one another when the pinch zone is in the expanded configuration.

12. A slide clamp for use with a tube having a fluid passageway, the clamp including a plate having a longitudinal length and a transverse width, a slot disposed within the plate having a flow section dimensioned to allow free flow of fluid through the passageway, an occlusion section dimensioned to prevent free flow of fluid through the passageway, and a necked area interconnecting the non-occlusion section and the occlusion section, the necked area comprising:

a pair of curved beams having a space located therebetween;

a first position wherein the space between the curved beams has an unexpanded width narrower than a width of the occlusion section; and a second position wherein the curved beams flex to expand the width of the space to permit movement of the tube from the flow section to the occlusion section and from the occlusion section to the flow section when the tube is subjected to a force adequate to flex the curved beams;

wherein the curved beams being formed so that they flex back to the first position after the tube has moved through the space; and wherein the curved beams resist movement of the tube from the occlusion section to the flow section when the tube is subjected to a force inadequate to flex the curved beams.

13. The slide clamp of claim 12 further comprising a relief portion adjacent each curved beam for providing relief during flexing of the curved beam.

14. The slide clamp of claim 12 wherein the necked area has a flat surface for contacting the tube.

15. The slide clamp of claim 14 wherein the necked area surface is fabricated from a material having low friction surface properties.

16. The slide clamp of claim 12 wherein a surface of the occlusion section for contacting the tube is defined by an edge coming to a point.

17. The clamp of claim 16 wherein the occlusion section surface is fabricated from a material having low friction surface properties.

18. The slide clamp of claim 12 wherein the plate is made of a deformable and resilient material, the material has a resiliency to regain its original shape after being subjected to a force capable of deforming the material.

* * * * *